United States Patent [19]

Hackler et al.

[11] Patent Number: 5,338,742
[45] Date of Patent: Aug. 16, 1994

[54] NEMATICIDAL USE OF 4-ARALKYLPYRIDINES

[75] Inventors: Ronald E. Hackler, Indianapolis; Glen P. Jourdan; Leon N. Davis, both of Morristown, all of Ind.

[73] Assignee: DowElanco, Indianapolis, Ind.

[21] Appl. No.: 753,492

[22] Filed: Sep. 3, 1991

[51] Int. Cl.$^5$ .............................................. A01N 43/40
[52] U.S. Cl. ...................................... 514/277; 514/63; 514/342; 514/345; 514/348; 514/351; 514/352; 514/357
[58] Field of Search .................. 514/277, 63, 345, 348, 514/347, 351, 352, 357

[56] References Cited

U.S. PATENT DOCUMENTS 3,983,107 9/1976 Holland .............................. 260/240
4,883,789 11/1989 Sieburth ............................. 514/63

FOREIGN PATENT DOCUMENTS

90/02736 3/1990 PCT Int'l Appl. .
932643 7/1963 United Kingdom ................ 514/277
1141707 1/1969 United Kingdom .
9002736 3/1990 World Int. Prop. O. .

OTHER PUBLICATIONS

H. Pines, et al. "Base-Catalyzed Reactions XXXIV," *J. Org. Chem.*, vol. 34, pp. 2113–2118 (Jul. 1969).

Derwent Abstract 30248-C, abstracting JA 7116106 (1971).
K. C. Crook, "Preparation of 2- and 4-Benzypyridine," *J.A.C.S.*, vol. 70, pp. 416–417 (1948).
Hideo Takeshiba, et al., "Benzylpyridine," *Ann. Sankyo Res. Lab.*, vol. 23, pp. 225–232 (1971).
Derwent Abstract 86-121849/19, abstracting JP 61060651A (1986).
CA Selects: Insecticides, Issue 23 (1988), abstract No. 109:165735a, abstracting JP 6333305.
CA Selects: Novel Pesticides & Herbicides, Issue 19 (1989), p. 6, abs. No. 111:77855a, abstracting EP 302,366.
CA Selects: Novel Pesticides & Herbicides, Issue 19 (1989), p. 7, abst. No. 111:77856b , abstracting EP 302,365.
Chemical Abstracts, vol. 113, pp. 633–634, abst. 113:132010q, abstracting PCT appln. WO90 02,736 (1990).
Derwent Abstracts 90-115943/15, abstracting PCT appln. WO90 02,736 (1990).

*Primary Examiner*—Richard L. Raymond
*Attorney, Agent, or Firm*—Donald R. Stuart

[57] ABSTRACT

4-Aralkylpyridines, for example 4-[3-[4-[(1-methylethyl)oxy]phenyl]propyl]pyridine, are active against nematodes.

23 Claims, No Drawings

NEMATICIDAL USE OF 4-ARALKYLPYRIDINES

FIELD OF THE INVENTION

This invention provides a new nematicidal method. It also provides novel compounds.

There is an acute need for new nematicides. Available nematicides typically must be used at high rates and have high mammalian toxicity. A nematicide that can be applied at lower rates and that has lower mammalian toxicity would represent a significant advance.

Derwent Abstract 90-115943/15, abstracting PCT Int. Appl. WO 90 02,736 discloses certain 4-aralkylpyridines as insecticides and miticides, but does not disclose or suggest that such compounds might exhibit exceptional nematicidal activity.

SUMMARY OF THE INVENTION

This invention provides a method of inhibiting a nematode population which comprises applying to the locus of a nematode, a nematode inactivating amount of a compound of the formula (1):

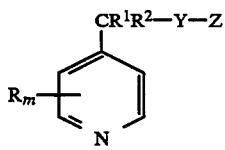

(1)

or an N-oxide thereof, wherein

R is halo, $(C_1-C_4)$ alkyl, $(C_3-C_4)$ branched alkyl, $(C_1-C_4)$ alkoxy, halo $(C_1-C_4)$ alkyl, $(C_1-C_4)$ alkylthio, $(C_1-C_4)$ alkylsulfinyl, $(C_1-C_4)$ alkylsulfonyl, aryl, or substituted amino;

m is 0 or 1 if R is other than halo and m is 1–4 if R is halo; each R may be the same or different if m is greater than 1;

$R^1$ and $R^2$ are independently H, $(C_1-C_4)$ alkyl, $(C_2-C_4)$ alkenyl or alkynyl, CN, or OH, or $R^1$ and $R^2$ combine to form a carbocyclic ring containing four to six carbon atoms;

Y is a bivalent hydrocarbon radical one to six carbon atoms long, optionally substituted with one or more groups independently selected from $(C_1-C_4)$ alkyl, $(C_2-C_4)$ alkenyl or $(C_3-C_7)$ alkynyl, branched $(C_3-C_7)$ alkyl, $(C_3-C_7)$ cycloalkyl $(C_3-C_7)$ cycloalkenyl, halo, halo $(C_1-C_4)$ alkyl, halo $(C_1-C_4)$ alkoxy, hydroxy, or $(C_1-C_4)$ acyl; and Z is
(a) aryl or
(b) $(C_3-C_8)$ cycloalkyl or cycloalkenyl, optionally substituted with one or more groups independently selected from $(C_1-C_4)$ alkyl, $(C_1-C_4)$ alkoxy, halo $(C_1-C_4)$ alkyl, halo $(C_1-C_4)$ alkoxy, halo, hydroxy, or $(C_1-C_4)$ acyl; and aryl is
(a) a phenyl group optionally substituted with one or more groups independently selected from:
halo,
$(C_3-C_8)$ cycloalkyl,
$(C_3-C_8)$ cycloalkenyl,
phenoxy,
substituted phenoxy,
phenylthio,
substituted phenylthio,
phenyl,
substituted phenyl,
$NO_2$,

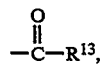

where $R^{13}$ is $(C_1-C_7)$ alkyl, halo $(C_1-C_7)$ alkyl, $(C_3-C_7)$ branched alkyl, halo $(C_3-C_7)$ branched alkyl, $(C_3-C_7)$ cycloalkyl, halo $(C_3-C_7)$ cycloalkyl, phenyl, or substituted phenyl,
acetoxy,
OH,
CN,
$SiR^3R^4R^5$ or $OSiR^3R^4R^5$, where $R^3$, $R^4$ and $R^5$ are independently $(C_1-C_4)$ alkyl, $(C_3-C_4)$ branched alkyl, phenyl, or substituted phenyl,
$NR^6R^7$, where $R^6$ and $R^7$ are independently H, $(C_1-C_4)$ alkyl, or $(C_1-C_4)$ acyl,
$S(O) R^8$, or $SO_2R^8$, where $R^8$ is $(C_1-C_{10})$ alkyl, phenyl, or substituted phenyl;
a $C_1-C_{12}$ saturated or unsaturated hydrocarbon chain, straight chain or branched optionally including a hetero atom selected from O, S, SO, $SO_2$, $NR^6$ or $SiR^3R^4$, where $R^3$ $R^4$, and $R^6$ are as defined above, and optionally substituted with halo, halo $(C_1-C_4)$ alkoxy, hydroxy, $(C_3-C_8)$ cycloalkyl or cycloalkenyl, $(C_1-C_4)$ acyl, phenoxy, substituted phenoxy, phenyl, substituted phenyl, phenylthio, or substituted phenylthio;
$(C_1-C_7)$ alkoxy optionally substituted with halo, phenyl, substituted phenyl, $(C_3-C_8)$ cycloalkyl or cycloalkenyl, phenoxy, or substituted phenoxy; or
$(C_1-C_7)$ alkylthio optionally substituted with halo, phenyl, substituted phenyl, $(C_3-C_8)$ cycloalkyl or cycloalkenyl, phenoxy or substituted phenoxy; (b) a furyl group of formula (3)

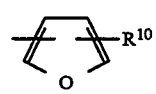

(3)

where $R^{10}$ is H, halo, halomethyl, CN, $NO_2$, $(C_1-C_4)$ alkyl, $(C_3-C_4)$ branched alkyl, phenyl, $(C_1-C_4)$ alkoxy;
(c) a thienyl group of the formula (4)

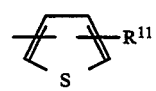

(4)

where $R^{11}$ is H, halo, halomethyl, CN, $NO_2$, $(C_1-C_4)$ alkyl, $(C_3-C_4)$ branched alkyl, phenyl $(C_1-C_4)$ alkoxy, or thienyl;
(d) a group of formula (5) or (6)

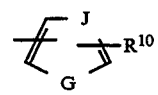

(5)

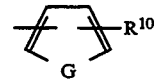

(6)

where $R^{10}$ is as defined in paragraph (b), J is N or CH, and G is O, $NR^{12}$, or S, provided that if J is not N then G is NR, where $R^{12}$ is H, ($C_1$–$C_4$) alkyl, ($C_1$–$C_4$) acyl, phenylsulfonyl, or substituted phenylsulfonyl;

(e) a group selected from
    optionally substituted naphthyl, dihydronaphthyl, tetrahydronaphthyl, and decahydronaphthyl;
    optionally substituted pyridyl;
    optionally substituted indolyl;
    1,3-benzodioxolyl;
    2,6-dimethyl-4-morpholinyl; and
    1-adamantyl.

DETAILED DESCRIPTION OF THE INVENTION

Throughout this document, all temperatures are given in degrees Celcius, and all percentages are weight percentages unless otherwise stated.

The term "halo" refers to a F, Cl, Br, or I atom.

The terms "alkoxy", "haloalkyl", "alkylsulfinyl", and "alkylsulfonyl" refer to straight chain and branched chain groups.

The term "substituted phenyl" refers to phenyl substituted with up to three groups independently selected from halo, ($C_1$–$C_{10}$) alkyl, branched ($C_3$–$C_6$) alkyl, halo ($C_1$–$C_7$) alkyl, hydroxy ($C_1$–$C_7$) alkyl, ($C_1$–$C_7$) alkoxy, halo ($C_1$–$C_7$) alkoxy, phenoxy, substituted phenoxy, phenyl, substituted phenyl, $NO_2$, OH, CN, ($C_1$–$C_4$) alkanoyl, benzoyl, ($C_1$–$C_4$) alkanoyloxy, or benzoyloxy.

The terms "substituted naphthyl", "substituted pyridyl" and "substituted indolyl" refer to these ring systems substituted with one or more groups independently selected from halo, halo ($C_1$–$C_4$) alkyl, CN, $NO_2$, ($C_1$–$C_4$) alkyl, ($C_3$–$C_4$) branched alkyl, phenyl, ($C_1$–$C_4$) alkoxy, or halo ($C_1$–$C_4$) alkoxy.

The term "substituted phenoxy" refers to phenoxy substituted with up to three groups independently selected from halo, I, ($C_1$–$C_{10}$) alkyl, branched ($C_3$–$C_6$) alkyl, halo ($C_1$–$C_7$) alkyl, hydroxy ($C_1$–$C_7$) alkyl, ($C_1$–$C_7$) alkoxy, halo ($C_1$–$C_7$) alkoxy, phenoxy, substituted phenoxy, phenyl, substituted phenyl, $NO_2$, OH, CN, ($C_1$–$C_4$) alkanoyloxy, or benzoyloxy.

The term "carbocyclic ring" refers to a saturated or unsaturated carbocyclic ring containing three to seven carbon atoms.

The terms "substituted phenylthio" and "substituted phenyl sulfonyl" refer to such groups substituted with up to three groups independently selected from halo, ($C_1$–$C_{10}$) alkyl, branched ($C_3$–$C_6$) alkyl, halo ($C_1$–$C_7$) alkyl, hydroxy ($C_1$–$C_7$) alkyl ($C_1$–$C_7$) alkoxy, halo ($C_1$–$C_7$) alkoxy, phenoxy, substituted phenoxy, phenyl, substituted phenyl, $NO_2$, OH, CN, ($C_1$–$C_4$) alkanoyloxy, or benzoyloxy.

The term "unsaturated hydrocarbon chain" refers to a hydrocarbon chain containing one or more sites of unsaturation.

The term "HPLC" refers to a high pressure liquid chromatography.

The term "bivalent hydrocarbon radical" refers to bivalent radicals derived from normal alkanes by removal of hydrogen atoms from each of the two terminal carbon atoms of the chain, e.g. methylene, ethylene, trimethylene, tetramethylene, etc.

The term "substituted amino" refers to an amino group that is substituted with one or two ($C_1$–$C_4$) alkyl groups or one ($C_1$–$C_4$) alkanoyl group.

Unless otherwise indicated, when it is stated that a group may be substituted with one or more substituents selected from an identified class, it is intended that the substituents may be independently selected from the class.

PREFERRED EMBODIMENTS

While the compounds of formula (1) are believed to be generally useful in the nematicidal method of this invention, certain classes of compounds are preferred for reasons of greater efficacy or ease of synthesis, viz:

a) compounds of formula (1) wherein Y is —$CH_2CH_2$—;

b) compounds of formula (1) wherein Z is phenyl;

c) compounds of formula (1) wherein Z is a substituted phenyl group as defined in paragraph (a) of the foregoing definition of "aryl;"

d) compounds of formula (1) wherein Z is a phenyl group substituted with a ($C_2$–$C_4$) alkoxy group;

e) compounds of formula (1) wherein Z is a phenyl group substituted with a ($C_3$–$C_7$) branched alkoxy group;

f) compounds of formula (1) wherein Z is a phenyl group substituted with a halo($C_2$–$C_4$) alkoxy group;

g) compounds of formula (1) wherein Z is a phenyl group substituted with a halo ($C_3$–$C_7$) branched alkoxy group;

h) compounds of formula (1) wherein Z is a phenyl group substituted with a phenoxy or substituted phenoxy group.

i) compounds of any of the foregoing groups c) to h) wherein the phenyl group is monosubstituted in the 4-position.

SYNTHESIS

The compounds utilized in this invention are made using well known chemical procedures. The required starting materials are commercially available, or they are readily synthesized using standard procedures.

For example, the compounds of formula (1) wherein $CR^1R^2$ is $CH_2$ can be made using the process described in the *J. Heterocyclic Chemistry*, Vol. 14, 1081–1083 (1977). This procedure involves hydrolysis and decarboxylation of 5-substituted-5-(4-pyridyl)-barbituric acids of the formula

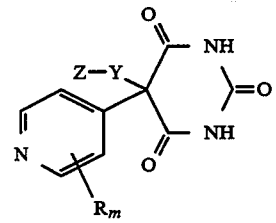

wherein the variable substituents are as defined for formula (1). The 5-substituted-5-(4-pyridyl)-barbituric acid is dissolved in a solution of sodium hydroxide and water and refluxed. The solution is then made slightly acidic and again refluxed.

Compounds of formula (1) may also be prepared by reacting a compound of formula (2)

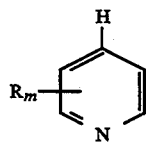

(2)

with a Grignard reagent of the formula Z-Y-CR$^1$R$^2$-MgX' or a lithio reagent of the formula Z-Y-CR$^1$R$^2$-Li, where X' is halo, to provide a 3,4-dihydropyridine which is then oxidized to provide a compound of the invention. Typical reaction conditions are those described in Armarego and Smith, *J. Chem. Soc.*, page 5360 (1965).

A preferred procedure for preparing compounds of formula (1) is illustrated in the following scheme

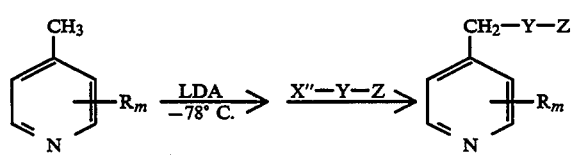

wherein X" is Cl, Br, or I, and Rm, Y, and Z are as defined above. In a typical prparation, 1 equivalent of a 4-methylpyridine is dissolved in 10 to 100 volumes of anhydrous tetrahydrofuran or other ether, and the mixture is stirred while cooling to −60° to −80° C. One equivalent of lithium diisopropyl amide (LDA) is added, and the mixture is stirred at the reduced temperature for 10 to 60 minutes. The mixture is allowed to warm to −10° C. over 1 to 2 hours, then cooled again to −60° to −80° C. A solution of 1 equivalent of the halide X"-Y-Z in 10 to 100 volumes of tetrahydrofuran is then added dropwise to the mixture while maintaining the reduced temperature. After 10 to 60 minutes the mixture is allowed to warm to room temperature. 10 to 300 volumes of water are added to the mixture, then the solvent is removed under vacuum. The residue is extracted with 10 to 200 volumes of an organic solvent such as ethyl acetate, ether, or methylene chloride. The resulting solution is dryed over a drying agent such as anhydrous magnesium sulfate, and concentrated under vacuum. The product may be purified by recrystallization, distillation, or chromatography.

DERIVATIVES

Compounds of formula (1) can be chemically modified using conventional techniques to provide other compounds of formula (1). For example, compounds of the formula

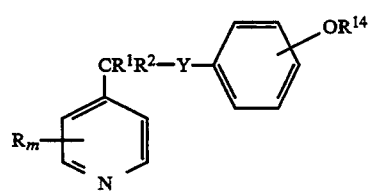

where R and m are as defined above and R$^{14}$ is a(C$_1$–C$_7$) saturated or unsaturated hydrocarbon radical, straight chain or branched, optionally substituted with hydroxy or one or more halo atoms, can be prepared by reacting a compound of the formula

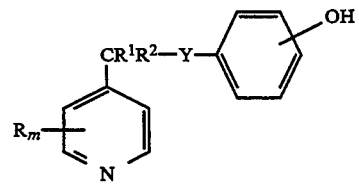

with sodium hydroxide and a compound of the formula BrR$^{14}$.

The N-oxides of compounds of formula (1) are obtained in the usual way. For example, the N-oxide can be obtained by oxidizing a compound of formula (1) with hydrogen peroxide in glacial acetic acid.

EXAMPLES

The following compounds of formula (1) were prepared by the above described general procedures. Specific illustrative preparations for the compounds of representative compounds follow the tabular listing.

| Example | CR$^1$R$^2$ | Y | Z | MP °C. |
|---|---|---|---|---|
| Example 1 | CH$_2$ | (CH$_2$)$_2$ | —⟨C$_6$H$_4$⟩—O(C$_4$H$_9$) | |
| Example 2 | CH$_2$ | (CH$_2$)$_2$ | —⟨C$_6$H$_4$⟩ (OCH$_3$ meta) | oil |
| Example 3 | CH$_2$ | (CH$_2$)$_2$ | —⟨C$_6$H$_4$⟩—Cl | oil |
| Example 4 | CH$_2$ | (CH$_2$)$_2$ | —⟨C$_6$H$_4$⟩—OCH$_3$ | |
| Example 5 | CH$_2$ | (CH$_2$)$_2$ | —⟨C$_6$H$_4$⟩—O(C$_2$H$_5$) | 79–81 |
| Example 6 | CH$_2$ | (CH$_2$)$_2$ | —⟨C$_6$H$_4$⟩—C(CH$_3$)$_3$ | oil |
| Example 7 | CH$_2$ | (CH$_2$)$_2$ | —⟨C$_6$H$_4$⟩—O(CH$_2$)$_2$CH(CH$_3$)$_2$ | oil |
| Example 8 | CH$_2$ | CH$_2$ | —⟨C$_6$H$_4$⟩ (CH$_3$ meta) | |
| Example 9 | CH$_2$ | (CH$_2$)$_2$ | —⟨C$_6$H$_4$⟩—OCH(CH$_3$)$_2$ | oil |
| Example 10 (N-oxide) | CH$_2$ | (CH$_2$)$_2$ | —⟨C$_6$H$_4$⟩—C(CH$_3$)$_3$ | 76–77 |
| Example 11 | CH$_2$ | (CH$_2$)$_2$ | —⟨C$_6$H$_4$⟩—O—⟨C$_6$H$_4$⟩—Cl | oil |
| Example 12 | CH$_2$ | (CH$_2$)$_2$ | —⟨C$_6$H$_4$⟩—O—⟨C$_6$H$_5$⟩ | oil |

-continued

| Example | CR¹R² | Y | Z | MP °C. |
|---|---|---|---|---|
| Example 13 | CH₂ | (CH₂)₂ | 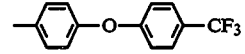 | 5 |
| Example 14 | CH₂ | (CH₂)₂ | 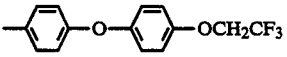 | |

The compounds were characterized by ¹H NMR. All values were determined in CDCl₃ and recorded as ∂ (ppm).

| Compound Example No. | Analysis |
|---|---|
| Example 1 | .097 (t, 3 H), 1.49 (m, 2 H), 1.76 (m, 2 H), 1.93 (m, 2 H), 2.59 (m, 4 H), 6.83 (d, 2 H), 7.10 (m, 4 H), 8.49 (d, 2 H) |
| Example 2 | 1.95 (m, 2 H), 2.62 (t, 4 H), 3.79 (s, 3 H), 6.72–7.21 (m, 6 H), 8.48 (d, 2 H) |
| Example 3 | 1.91 (m, 2 H), 2.62 (m, 4 H), 7.06–7.24 (m, 6H), 8.48 (d, 2 H) |
| Example 4 | 1.19 (m, 4 H), 3.79 (s, 3 H), 6.82–7.10 (m, 6 H), 8.48 (d, 2 H) |
| Example 6 | 1.31 (s, 9 H), 1.96 (m, 2 H), 2.62 (m, 4 H), 7.02–7.31 (m, 6 H), 8.48 (d, 2 H) |
| Example 7 | 0.95–0.97 (d, 6 H), 1.65–1.93 (m, 5 H), 2.6 (m, 4 H), 3.96 (t, 2 H), 6.83 (d, 2 H), 7.09 (m, 4 H), 8.48 (d, 2 H) |
| Example 8 | 2.31 (s, 3H), 2.88 (s, 4 H), 6.93–7.19 (m, 6 H), 8.46–8.48 (d, 2 H) |
| Example 9 | 1.37 (d, 6 H), 1.89–1.96 (m, 2 H), 2.55–2.64 (m, 4 H), 4.50 (m, 1 H), 6.82–7.10 (m, 6 H), 8.47 (d, 2 H) |

The procedures described in the following detailed Examples are representative of the procedures used to prepare the compounds of the other Examples.

EXAMPLE 1

4-[3-(4-butoxyphenyl)propyl]pyridine

Excess 1-bromobutane was added to a mixture of 0.9 g of 4-[3-(4-hydroxyphenyl)propyl]pyridine in 10 mL of 2N NaOH, and the mixture was refluxed for several hours. Then the mixture was cooled and the pH adjusted to 10. The product was extracted with CH₂Cl₂. The CH₂Cl₂ layer was then separated, washed with fresh water, filtered through phase separating paper, and concentrated. The residue was adsorbed onto silica gel and chromatographed over silica gel eluting with CH₂Cl₂ > 15% EtOAc/CH₂Cl₂. Yield 0.45 g.

EXAMPLE 3

4-[3-(4-chlorophenyl)propyl]pyridine

A mixture of 3 g (0.02 m) of 4-chloropyridine hydrochloride and 5.3 g (0.02 m) of 5-[2-(4-chlorophenyl)ethyl]barbituric acid was thoroughly mixed with a mortar and pestle, heated in a 200° C. oil bath for 15–20 minutes, and then cooled. To the resulting product was added 5 g of NaOH and 40 mL of water, and the mixture was refluxed for several hours. After cooling the mixture, it was acidified with concentrated HCl, again refluxed for 45 minutes, and then cooled. The resulting material was diluted into water; the pH of the aqueous solution was adjusted to 7–8 with dilute NaOH; then the product was extracted into CH₂Cl₂. The CH₂Cl₂ layer was separated, filtered through phase separating paper, and concentrated. The residue was adsorbed onto silica gel and chromatographed using 5% EtOAc/CH₂Cl₂ > 10% EtOAc/CH₂Cl₂ > 5% MeOH/EtOAc (wash). Yield 0.82 g.

EXAMPLE 5

4-[3-(4-Ethoxyphenyl)propyl]pyridine

A mixture of 6.5 g (0.0235 m) of 5-[2-(4-ethoxyphenyl)ethyl]barbituric acid and 7 g (0.047 m) of 4-chloropyridine hydrochloride was mixed with a mortar and pestle and heated in an oil bath until the reagents formed a melt (185° C.). The mixture was kept at 180°–185° for 15–20 minutes, when the mixture began to noticeably darken. When heat was removed, the mixture quickly formed a hard glass. To this product, 6.5 g of NaOH pellets and 40 mL of water was added, and the mixture was refluxed for 5–6 hours. After cooling, the mixture was acidified with concentrated HCl and refluxed for 1½ hours. The mixture was then diluted over ice, and the pH was adjusted to neutral using dilute NaOH. The product was then extracted into CH₂Cl₂. The CH₂Cl₂ layer was separated, dried, adsorbed onto silica gel, and chromatographed using CH₂Cl₂ > 50% EtOAc/CH₂Cl₂. The product was an oil which crystallized. Yield 0.5 g. MP 79°–81° C.

EXAMPLE 11

4-(3-(4-(4-chlorophenoxy)phenyl)propyl)pyridine

To 0.308 g. of picoline in 20 mL of tetrahydrofuran, which was cooled to −78° C., was added 1.6 mL of lithium diisopropyl amide, and the mixture was stirred at −78° C. for 30 minutes. The mixture was then allowed to warm to −10° C. for 2 hours, then cooled again to −78° C. There was then added a solution of 1.0 g. of 1-(4-chlorophenoxy)-4-(2-bromoethyl)benzene in 20 mL of tetrahydrofuran. This mixture was stirred for 30 minutes at −78° C., then allowed to warm to room temperature and stirred overnight. 50 mL of water was added dropwise and the tetrahydrofuran was removed by reducing pressure. The residue was extracted with ethyl acetate, which was concentrated to dryness. The product was purified by HPLC (silica gel 70% pentane; 30% ethyl acetate over 180 minutes) to give 0.107 g. of an oil.

NEMATICIDE UTILITY

The compounds of the present invention are useful for reducing populations of nematodes. Accordingly, another aspect of the invention is a method of inhibiting a nematode population which comprises applying to a locus of a nematode a nematode inactivating amount of a compound of formula (1). The term "inhibiting a nematode" refers to a decrease in the numbers of living nematodes. The extent of reduction accomplished by a compound depends, of course, upon the application rate of the compound, the particular compound used, and the target species. At least a nematode-inactivating amount should be used. The term "nematode-inactivating amount" is used to describe the amount, which is sufficient to cause a measurable reduction in the treated nematode population.

The method is practiced in accordance with standard techniques for the application of nematicides. In general, good nematicidal activity can be expected at rates of 1–10 lbs/acre. The compound can be formulated as described below in the Formulations section.

Compounds were tested against the peanut root knot nematode, *Meloidogyne arenaria* in the peanut root knot nematode assay. The peanut root knot nematode assay is carried out as follows. Each test compound is initially formulated as a 400 ppm solution by combining 19.2 mL of 0.05% Solution of Tween 20 (polyoxyethylene (20) sorbitan monolaurate) in water with a solution of 8 mg of the compound in 0.8 mL of acetone/EtOH (9/1). The 400 ppm solution is then diluted with water to give the necessary concentration. Three to four cucumber seeds are placed in 16 g of clean white sand, and 1 mL of the solution of test compound is added. A 200 ppm solution provides a concentration of the compound in the sand of 12 ppm. The cups are allowed to dry one to two hours, and then one mL of a concentrated (50 to 60 per mL) nematode (*Meloidogyne arenaria*) suspension is added to each cup. The cups are incubated for four to seven Gays. Then 11 mL of deionized water is added to each cup and the cup is gently shaken to rinse the nematodes from the sand. The suspension is poured into a watchglass and observed under a dissecting microscope at 15x–20x. An activity rating is given based on nematode mortality. Aldicarb, carbofuran, and fenamiphos are used as chemical standard compounds. Results are reported in the following table. The "rate" referred to in the table is the concentration of test compound in sand.

| Compound Ex. No. | Rate in ppm | Results % Control |
|---|---|---|
| 1 | 12.00 | 100.00 |
|   | 12.00 | 100.00 |
|   | 6.00 | 70.00 |
|   | 3.00 | 15.00 |
| 4 | 12.00 | 100.00 |
|   | 12.00 | 100.00 |
|   | 6.00 | 70.00 |
|   | 3.00 | 20.00 |
|   | 1.50 | 0.00 |
| 5 | 12.00 | 100.00 |
|   | 12.00 | 100.00 |
|   | 6.00 | 100.00 |
|   | 3.00 | 35.00 |
|   | 1.50 | 0.00 |
| 6 | 12.00 | 70.00 |
|   | 6.00 | 0.00 |
| 7 | 12.00 | 100.00 |
|   | 12.00 | 100.00 |
|   | 6.00 | 70.00 |
|   | 3.00 | 30.00 |
|   | 1.50 | 0.00 |
| 8 | 12.00 | 0.00 |
| 9 | 12.00 | 100.00 |
|   | 3.00 | 90.00 |
|   | 1.50 | 50.00 |
|   | 0.75 | 35.00 |
|   | 0.38 | 0.00 |
| 10 | 12.00 | 100.00 |
|   | 12.00 | 100.00 |
|   | 6.00 | 80.00 |
|   | 3.00 | 20.00 |
|   | 1.50 | 0.00 |

The compounds of formula (1) also show activity against a number of insects and mites. More specifically, the compounds show activity against melon aphid, which is a member of the insect order Homoptera. Other members of the Homoptera include leafhoppers, planthoppers, pear pyslla, apple sucker, scale insects, whiteflies, spittle bugs as well as numerous other host specific aphid species. Activity has also been observed against greenhouse thrips, which are members of the order Thysanoptera. The compounds also show activity against Southern armyworm, which is a member of the insect order Lepidoptera. Other typical members of this order are codling moth, cutworm, clothes moth, Indian-meal moth, leaf rollers, corn earworm, European corn borer, cabbage worm, cabbage looper, cotton bollworm, bagworm, eastern tent caterpillar, sod webworm, and fall armyworm.

The compounds of formula (1) also have been found to control fungi, particularly plant pathogens.

COMPOSITIONS

The compounds of formula (1) are applied in the form of compositions which are important embodiments of the invention, and which comprise a compound of formula (1) and a phytologically-acceptable inert carrier. The compositions are either concentrated formulations which are dispersed in water for application, or are granular formulations which are applied without further treatment. The compositions are prepared according to procedures and formulae which are conventional in the agricultural chemical art, but which are novel and important because of the presence therein of the compounds of this invention. Some description of the formulation of the compositions will be given, however, to assure that agricultural chemists can readily prepare any desired composition.

The dispersions in which the compounds are applied are most often aqueous suspensions or emulsions prepared from concentrated formulations of the compounds. Such water-soluble, water-suspendable or emulsifiable formulations are either solids usually known as wettable powders, or liquids usually known as emulsifiable concentrates or aqueous suspensions. Wettable powders, which may be compacted to form water dispersible granules, comprise an intimate mixture of the active compound, an inert carrier and surfactants. The concentration of the active compound is usually from about 10% to about 90% by weight. The inert carrier is usually chosen from among the attapulgite clays, the montmorillonite clays, the diatomaceous earths, or the purified silicates. Effective surfactants, comprising from about 0.5% to about 10% of the wettable powder, are found among the sulfonated lignins, the condensed naphthalenesulfonates, the naphthalenesulfonates, the alkylbenzenesulfonates, the alkyl sulfates, and non-ionic surfactants such as ethylene oxide adducts of alkyl phenols.

Emulsifiable concentrates of the compounds comprise a convenient concentration of a compound, such as from about 50 to about 500 grams per liter of liquid, equivalent to about 10% to about 50%, dissolved in an inert carrier which is either a water miscible solvent or a mixture of water-immiscible organic solvent and emulsifiers. Useful organic solvents include aromatics, especially the xylenes, and the petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are chosen from conventional nonionic surfactants, such as those discussed above.

Aqueous suspensions comprise suspensions of water-insoluble compounds of this invention, dispersed in an aqueous vehicle at a concentration in the range from about 5% to about 50% by weight. Suspensions are prepared by finely grinding the compound, and vigorously mixing it into a vehicle comprised of water and surfactants chosen from the same types discussed above.

Inert ingredients, such as inorganic salts and synthetic or natural gums, may also be added, to increase the density and viscosity of the aqueous vehicle. It is often most effective to grind and mix the compound at the same time by preparing the aqueous mixture, and homogenizing it in an implement such as a sand mill, ball mill, or piston-type homogenizer.

The compounds may also be applied as granular compositions. Granular compositions usually contain from about 0.5% to about 10% by weight of the compound, dispersed in an inert carrier which consists entirely or in large part of clay or a similar inexpensive substance. Such compositions are usually prepared by dissolving the compound in a suitable solvent, and applying it to a granular carrier which has been pre-formed to the appropriate particle size, in the range of from about 0.5 to 3 mm. Such compositions may also be formulated by making a dough or paste of the carrier and compound, and crushing and drying to obtain the desired granular particle size.

It is equally practical, when desirable for any reason, to apply the compound in the form of a solution in an appropriate organic solvent, usually a bland petroleum oil, such as the spray oils, which are widely used in agricultural chemistry.

Nematicides are generally applied in the form of a dispersion of the active ingredient in a liquid carrier. It is conventional to refer to application rates in terms of the concentration of active ingredient in the carrier. The most widely used carrier is water.

The compounds of formula (1) can also be applied in the form of an aerosol composition. In such compositions the active compound is dissolved or dispersed in an inert carrier, which is a pressure-generating propellant mixture. The aerosol composition is packaged in a container from which the mixture is dispensed through an atomizing valve. Propellant mixtures comprise either low-boiling halocarbons, which may be mixed with organic solvents, or aqueous suspensions pressurized with inert gases or gaseous hydrocarbons.

The following formulations of compounds of the invention are typical of compositions useful in the practice of the present invention.

| A. 0.75 Emulsifiable Concentrate | |
|---|---|
| Compound of Example 9 | 9.38% |
| "TOXIMUL D" | 2.50% |
| (nonionic/anionic surfactant blend) | |
| "TOXIMUL H" | 2.50% |
| (nonionic/anionic surfactant blend) | |
| "EXXON 200" | 85.62% |
| (naphthalenic solvent) | |
| B. 1.5 Emulsifiable Concentrate | |
| Compound of Example 4 | 18.50% |
| "TOXIMUL D" | 2.50% |
| "TOXIMUL H" | 2.50% |
| "EXXON 200" | 76.50% |
| C. 1.0 Emulsifiable Concentrate | |
| Compound of Example 5 | 12.50% |
| N-methylpyrrolidone | 25.00% |
| "TOXIMUL D" | 2.50% |
| "TOXIMUL H" | 2.50% |
| "EXXON 200" | 57.50% |
| D. 1.0 Aqueous Suspension | |
| Compound of Example 9 | 12.00% |
| "PLURONIC P-103" | 1.50% |
| (block copolymer of propylene oxide and ethylene oxide, surfactant) | |
| "PROXEL GXL" | .05% |
| (biocide/preservative) | |
| "AF-100" | .20% |

| -continued | |
|---|---|
| (silicon based antifoam agent) | |
| "REAX 88B" | 1.00% |
| (lignosulfonate dispersing agent) | |
| propylene glycol | 10.00% |
| veegum | .75% |
| xanthan | .25% |
| water | 74.25% |
| E. 1.0 Aqueous Suspension | |
| Compound of Example 6 | 12.50% |
| "MAKON 10" (10 moles ethyleneoxide nonylphenol surfactant) | 1.00% |
| "ZEOSYL 200" (silica) | 1.00% |
| "AF-100" | 0.20% |
| "AGRIWET FR" (surfactant) | 3.00% |
| 2% xanthan hydrate | 10.00% |
| water | 72.30% |
| F. 1.0 Aqueous Suspension | |
| Compound of Example 7 | 12.50% |
| "MAKON 10" | 1.50% |
| "ZEOSYL 200" (silica) | 1.00% |
| "AF-100" | 0.20% |
| "POLYFON H" | 0.20% |
| (lignosulfonate dispersing agent) | |
| 2% xanthan hydrate | 10.00% |
| water | 74.60% |
| G. Wettable Powder | |
| Compound of Example 6 | 25.80% |
| "POLYFON H" | 3.50% |
| "SELLOGEN HR" | 5.00% |
| "STEPANOL ME DRY" | 1.00% |
| gum arabic | 0.50% |
| "HISIL 233" | 2.50% |
| Barden clay | 61.70% |

We claim:

1. A method of inhibiting a nematode population which comprises applying to nematodes or an infested locus thereof, a nematode inactivating amount of a compound of the formula (1):

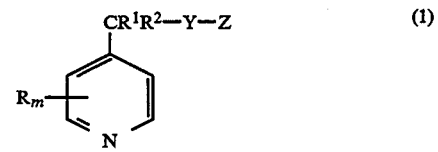

or an N-oxide thereof, wherein

R is halo, $(C_1-C_4)$ alkyl, $(C_3-C_4)$ branched alkyl, $(C_1-C_4)$ alkoxy, halo $(C_1-C_4)$ alkyl, $(C_1-C_4)$ alkylthio, $(C_1-C_4)$ alkylsulfinyl, $(C_1-C_4)$ alkylsulfonyl, or substituted amino;

m is 0 or 1 if R is other than halo and m is 1–4 if R is halo; each R may be the same or different if m is greater than 1;

$R^1$ and $R^2$ are independently H, $(C_1-C_4)$ alkyl, $(C_2-C_4)$ alkenyl or alkynyl, CN, or OH, or $R^1$ and $R^2$ combine to form a carbocyclic ring containing four to six carbon atoms;

Y is a bond or a bivalent hydrocarbon radical one to six carbon atoms long, unsubstituted or substituted with one or more groups independently selected from $(C_1-C_4)$ alkyl, $(C_2-C_4)$ alkenyl or $(C_3-C_7)$ alkynyl, branched $(C_3-C_7)$ alkyl, $(C_3-C_7)$ cycloalkyl $(C_3-C_7)$ cycloalkenyl, halo, halo $(C_1-C_4)$ alkyl, halo $(C_1-C_4)$ alkoxy, hydroxy, or $(C_1-C_4)$ acyl; and Z is a phenyl group or a phenyl group substituted with one or more groups independently selected from:
halo,
$(C_3-C_8)$ cycloalkyl,
$(C_3-C_8)$ cycloalkenyl, phenoxy,
substituted phenoxy,
phenylthio,
substituted phenylthio,
phenyl,
substituted phenyl,
NO$_2$,

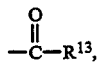

where R$^{13}$ is (C$_1$–C$_7$) alkyl, halo (C$_1$–c$_7$) alkyl, (C$_3$–C$_7$) branched alkyl, halo (C$_3$–C$_7$) branched alkyl, (C$_3$–C$_7$)cycloalkyl, halo (C$_3$–C$_7$) cycloalkyl, phenyl, or substituted phenyl,
acetoxy,
OH,
CN,
SiR$^3$R$^4$R$^5$ or OSiR$^3$R$^4$R$^5$, where R$^3$,R$^4$ and R$^5$ are independently (C$_1$–C$_4$) alkyl, (C$_3$–C$_4$) branched alkyl, phenyl, or substituted phenyl,
NR$^6$R$^7$, where R$^6$ and R$^7$ are independently H, (C$_1$–C$_4$) alkyl, or (C$_1$–C$_4$) acyl,
S(O) R$^8$, or SO$_2$R$^8$, where R$^8$ is (C$_1$–C$_{10}$) alkyl, phenyl, or substituted phenyl;
a C$_1$–C$_{12}$ saturated or unsaturated hydrocarbon chain, straight chain or branched, including or not including a hetero atom selected from O, S, SO, SO$_2$, NR$^6$, or SiR$^3$R$^4$, where R$^3$, R$^4$, and R$^6$ are as defined above, and unsubstituted or substituted with halo, halo (C$_1$–C$_4$) alkoxy, hydroxy, (C$_3$–C$_8$) cycloalkyl or cycloalkenyl, (C$_1$–C$_4$) acyl, phenoxy, substituted phenoxy, phenyl, substituted phenyl, phenylthio, or substituted phenylthio;
(C$_1$–C$_7$) alkoxy unsubstituted or substituted with halo, phenyl, substituted phenyl, (C$_3$–C$_8$) cycloalkyl or cycloalkenyl, phenoxy, or substituted phenoxy; or
(C$_1$–C$_7$) alkylthio unsubstituted or substituted with halo, phenyl, substituted phenyl, (C$_3$–C$_8$) cycloalkyl or cycloalkenyl, phenoxy or substituted phenoxy.

2. The method of claim 1 wherein the compound of formula (1) is one wherein Y is —(CH$_2$)$_2$—.

3. The method of claim 1 wherein the compound of formula (1) is a compound of formula (1) wherein Z is phenyl.

4. The method of claim 1 wherein the compound of formula (1) is one wherein Z is a phenyl group substituted with a (C$_2$–C$_4$) alkoxy group.

5. The method of claim 1 wherein the compound of formula (1) is one wherein Z is a phenyl group substituted with a (C$_3$–C$_7$) branched alkoxy group.

6. The method of claim 1 wherein the compound of formula (1) is one wherein Z is a phenyl group substituted with a halo(C$_2$–C$_4$) alkoxy group.

7. The method of claim 1 wherein the compound of formula (1) is one wherein Z is a phenyl group substituted with a halo (C$_3$–C$_7$)branched alkoxy group.

8. The method of claim 1 wherein the compound of formula (1) is one wherein Z is a phenyl group substituted with a phenoxy or substituted phenoxy group.

9. The method of claim 1 wherein the compound of formula (1) is one wherein Z is a phenyl group monosubstituted in the 4-position.

10. The method of claim 1 wherein the compound of formula (1) is one wherein Z is 4-(n-butoxy)phenyl.

11. The method of claim 1 wherein the compound of formula (1) is one wherein Z is 3-methoxyphenyl.

12. The method of claim 1 wherein the compound of formula (1) is one wherein Z is 4-chlorophenyl.

13. The method of claim 1 wherein the compound of formula (1) is one wherein Z is 4-methoxyphenyl.

14. The method of claim 1 wherein the compound of formula (1) is one wherein Z is 4-ethoxyphenyl.

15. The method of claim 1 wherein the compound of formula (1) is one wherein Z is 4-(t-butyl)phenyl.

16. The method of claim 1 wherein the compound of formula (1) is one wherein Z is 4-[(3-methylbutyl)oxy]phenyl.

17. The method of claim 1 wherein the compound of formula (1) is one wherein Z is 3-methylphenyl.

18. The method of claim 1 wherein the compound of formula (1) is one wherein Z is 4-[(isopropyl)oxy]phenyl.

19. The method of claim 1 wherein the compound of formula (1) is one wherein Z is 4-(4-chlorophenoxy)phenyl.

20. The method of claim 1 wherein the compound of formula (1) is one where in Z is 4-phenoxyphenyl.

21. The method of claim 1 wherein the compound of formula (1) is one wherein Z is 4-[4-(trifluromethoxy)phenoxy]phenyl.

22. The method of claim 1 wherein the compound of formula (1) is one wherein Z is 4-[4-(2,2,2-trifluroethoxy)-phenoxy]phenyl.

23. The method of claim 1 wherein the compound of formula (1) is 4-[3-[4-[(1-methylethyl)oxy]phenyl]-propyl]-pyridine.

* * * * *